United States Patent [19]

Mancosu et al.

[11] Patent Number: 5,311,778
[45] Date of Patent: May 17, 1994

[54] PROCESS AND APPARATUS TO IDENTIFY THE PRESENCE OF STRUCTURAL CAVITIES IN SLEEVES FOR THE MANUFACTURE OF DRIVING BELTS

[75] Inventors: Federico Mancosu, Milan; Roberto Sgnaolin, Piovera; Roberto Zavaglio, Milan, all of Italy

[73] Assignee: Pirelli Prodotti Diversificati S.p.A., Milan, Italy

[21] Appl. No.: 793,733

[22] Filed: Nov. 21, 1991

[30] Foreign Application Priority Data

Nov. 21, 1990 [IT] Italy .................. 22126 A/90

[51] Int. Cl.⁵ ......................................... G01N 29/26
[52] U.S. Cl. ................................. 73/622; 73/634
[58] Field of Search ............... 73/634, 620, 627, 629, 73/622

[56] References Cited

U.S. PATENT DOCUMENTS

| | | | |
|---|---|---|---|
| 4,018,082 | 4/1977 | Manoliu et al. | 73/600 |
| 4,274,289 | 6/1981 | Weiss et al. | 73/618 |
| 4,289,033 | 9/1981 | Prause et al. | 73/622 |
| 4,562,738 | 1/1986 | Nakayama et al. | 73/622 |
| 4,577,502 | 3/1986 | Cunningham | 73/600 |
| 4,596,953 | 6/1986 | Nagasaka et al. | 73/622 |
| 4,599,900 | 7/1986 | Friedman | 73/622 |
| 4,750,368 | 6/1988 | Shearer et al. | 73/618 |

Primary Examiner—Hezron E. Williams
Assistant Examiner—Rose M. Finley
Attorney, Agent, or Firm—Stevens, Davis, Miller & Mosher

[57] ABSTRACT

A process and apparatus for identifying defects within the structure of a tubular sleeve used to make toothed belts, the sleeve, having a toothed inner surface 2a, is operatively mounted on rollers 5, 6 operable in rotation to move the sleeve transversely to the extension of the teeth 3. An ultrasonic emitting and receiving member 15 movable parallel to the rollers 5, 6 detects the presence of structural cavities 3a in the sleeve. An electronic processing unit 20 carries out the identification and memorization of the position of the structural cavities 3a on the longitudinal extension of the sleeve 2.

18 Claims, 3 Drawing Sheets

PROCESS AND APPARATUS TO IDENTIFY THE PRESENCE OF STRUCTURAL CAVITIES IN SLEEVES FOR THE MANUFACTURE OF DRIVING BELTS

CROSS REFERENCE TO RELATED APPLICATIONS

Copending U.S. application Ser. No. 07/792,876, filed on even date herewith (now U.S. Pat. No. 5,198,068), for PROCESS AND APPARATUS TO APPLY IDENTIFICATION INSCRIPTIONS ON SLEEVES MADE OF ELASTOMERIC MATERIAL IN THE MANUFACTURE OF DRIVING BELTS.

Copending U.S. application Ser. No. 07/793,731, filed on even date herewith, for PROCESS AND APPARATUS FOR HANDLING DRIVING BELTS IN AN AUTOMATED MANNER.

Copending U.S. application Ser. No. 07/793,840, filed on even date herewith (now U.S. Pat. No. 5,217,562), for MACHINE AND PROCESS FOR COILING AND WINDING TUBULAR SLEEVES OF ELASTOMERIC MATERIAL INCORPORATING REINFORCING FIBERS.

Copending U.S. application Ser. No. 07/793,732, filed on even date herewith, for PROCESS AND APPARATUS FOR THE INSPECTING JUNCTIONS IN SLEEVE LINING FABRICS FOR THE MANUFACTURE OF TOOTHED BELTS.

Copending U.S. application Ser. No. 07/792,880, filed on even date herewith (now U.S. Pat. No. 5,243,532), for PROCESS AND AUTOMATIC INSTALLATION FOR THE CONTROL OF THE QUALITY AND OF THE PRODUCTION OF TRANSMISSION BELTS.

Copending U.S. application Ser. No. 07/793,729, filed on even date herewith (now U.S. Pat. No. 5,247,463), for A PROCESS AND APPARATUS FOR INSPECTING THE GEOMETRICAL CONFIGURATION OF TOOTHED DRIVING ELEMENTS.

The disclosures of each of the above identified U.S. applications and patents are hereby incorporated by reference.

BACKGROUND OF THE INVENTION

The present invention relates to a process and an apparatus to identify the presence of structural cavities in sleeves for the manufacture of driving belts.

The invention is adapted to carry out quality control tests on sleeves for the production of driving belts of different kinds, such as toothed belts, flat grooved belts, toothed V-belts and so on.

In the course of the present description reference will be particularly made, by way of example only, to the test carried out on a sleeve for the manufacture of toothed belts.

It is known that toothed belts are obtained by a cutting operation carried out at several axially spaced circumferential lines on an axially elongated cylindrical tubular sleeve having a toothed inner surface.

This sleeve is made by wrapping at least a reinforcement layer incorporating a plurality of inextensible cords around a cylindrical grooved die which has negatively reproduced toothing on its outer surface and upon which one or more layers of elastomeric material are then superposed.

The semifinished product thus obtained is then submitted to a vulcanization process in an autoclave.

During the above operation the semifinished product, previously enclosed in a rubber coating sheath, undergoes a suitable heating by means of steam under pressure which is sent into the die and to the outside of the sheath surrounding the semifinished product.

Due to the steam pressure, the layers of elastomeric material are submitted to homogeneously-distributed centripetal compressive forces urging the elastomeric material to forcedly pass through the inextensible cord layer. Thus the elastomeric material will fill the grooves provided in the die, thereby creating the inner toothing on the finished sleeve.

It may however happen that, during the vulcanization step, the proper formation of teeth is impaired due to undesired infiltrations of steam and/or condensate between the elastomer layers of the semi-finished product.

These infiltrations give rise to cavities in the sleeve structure and in particular within the teeth and the presence of said cavities causes an alteration to the operating features and strength of the toothed belts that will be subsequently obtained from the above cutting operation.

The formation of cavities can also take place for other reasons, for example due to the development of gas resulting from an incorrect composition of the materials forming the elastomeric layers.

It is clear that when a belt having defects of the above described type is used, it could easily break thereby involving the risk of serious damages to the apparatus on which the belt itself is mounted.

In order to avoid these risks as much as possible, it is necessary that the sleeves produced and/or the belts subsequently obtained be submitted to suitable quality control tests or inspections.

At the present state of the art these inspections are merely based on the visual examination of the toothing by an operator.

As can be easily understood, these empirical inspecting methods offer insufficient reliability. In fact, the identification of possible cavities in the sleeve toothing depends to a great extent on the skill of the operator entrusted with the inspection and the care he or she puts in carrying out the operation.

It is also necessary to take into account the fact that the cavities can be of very small sizes, having a diameter smaller than half a millimeter.

In addition and above all, the mere visual evaluation of the toothed surface enables only cavities appearing on the surface itself to be identified, without offering the possibility of detecting those cavities that are incorporated internally in the elastomeric material.

It is also to be pointed out that the presently used inspection methodologies do not permit timely interventions in the cases in which the structural cavities are due to incorrect operation of the apparatuses used during the sleeve vulcanization step or to errors in the composition of the materials used.

The main object of the present invention is substantially to solve the problems of the known art, by a process and an apparatus enabling an accurate and reliable inspection of the toothing.

A further object of the invention is to provide a process and an apparatus capable of identifying and signalling the presence of structural cavities in the toothing in a very timely manner, when they are due to incorrect operation of the apparatuses adopted in the vulcanization processes or to wrong compositions of the materials used for the manufacture of the sleeves, in order to allow immediate interventions for the elimination of these anomalies.

SUMMARY OF THE INVENTION

The foregoing and further objects that will become more apparent in the course of the following description are substantially attained by a process for identifying the presence of structural cavities in sleeves for the manufacture of driving belts, characterized in that it comprises the following steps:

a) operatively mounting a sleeve on supporting and handling means;

b) moving the sleeve in a direction transverse to its longitudinal axis;

c) positioning an ultrasonic emitting and receiving member in an operating condition on one wall of the sleeve;

d) moving the ultrasonic emitting and receiving member in to a direction parallel to the sleeve axis, so that said emitting and receiving member may send ultrasonic signals through the sleeve to a first read point moving in a helical manner relative to the sleeve axis;

e) detecting and processing signals emitted from the ultrasonic emitting and receiving member in order to identify the presence of structural cavities in the sleeve;

f) detecting and storing the position of the ultrasonic emitting and receiving member on the longitudinal extension of the sleeve when the presence of structural cavities has been ascertained.

In accordance with the invention, the above process is put into practice by an apparatus for identifying the presence of structural cavities in sleeves for the manufacture of driving belts, characterized in that it comprises:

supporting means designed to operatively engage a sleeve;

first motion-imparting means cooperating with said supporting means so as to impart a continuous movement to the sleeve in a transverse direction to the longitudinal extension thereof;

at least one ultrasonic emitting and receiving member arranged to operate through the sleeve at a first read point, in order to detect the presence of structural cavities in the sleeve itself;

second motion-imparting means acting on the emitting and receiving member to impart a translatory movement to the same in a direction parallel to the sleeve axis, so that the first read point will move in a helical manner relative to the sleeve axis;

an electronic processing unit operatively connected to the ultrasonic emitting and receiving member as well as to the second motion-imparting means in order to identify the position on the longitudinal extension of the sleeve of the structural cavities detected by said emitting and receiving member.

BRIEF DESCRIPTION OF THE DRAWINGS

Further features and advantages will become more apparent from the detailed description of a preferred embodiment of a process and an apparatus for identifying the presence of structural cavities in sleeves for the manufacture of driving belts in accordance with the invention, given hereinafter by way of non-limiting example with reference to the accompanying drawings, in which.

DETAILED DESCRIPTION OF A PREFERRED EMBODIMENT

Figure 1:
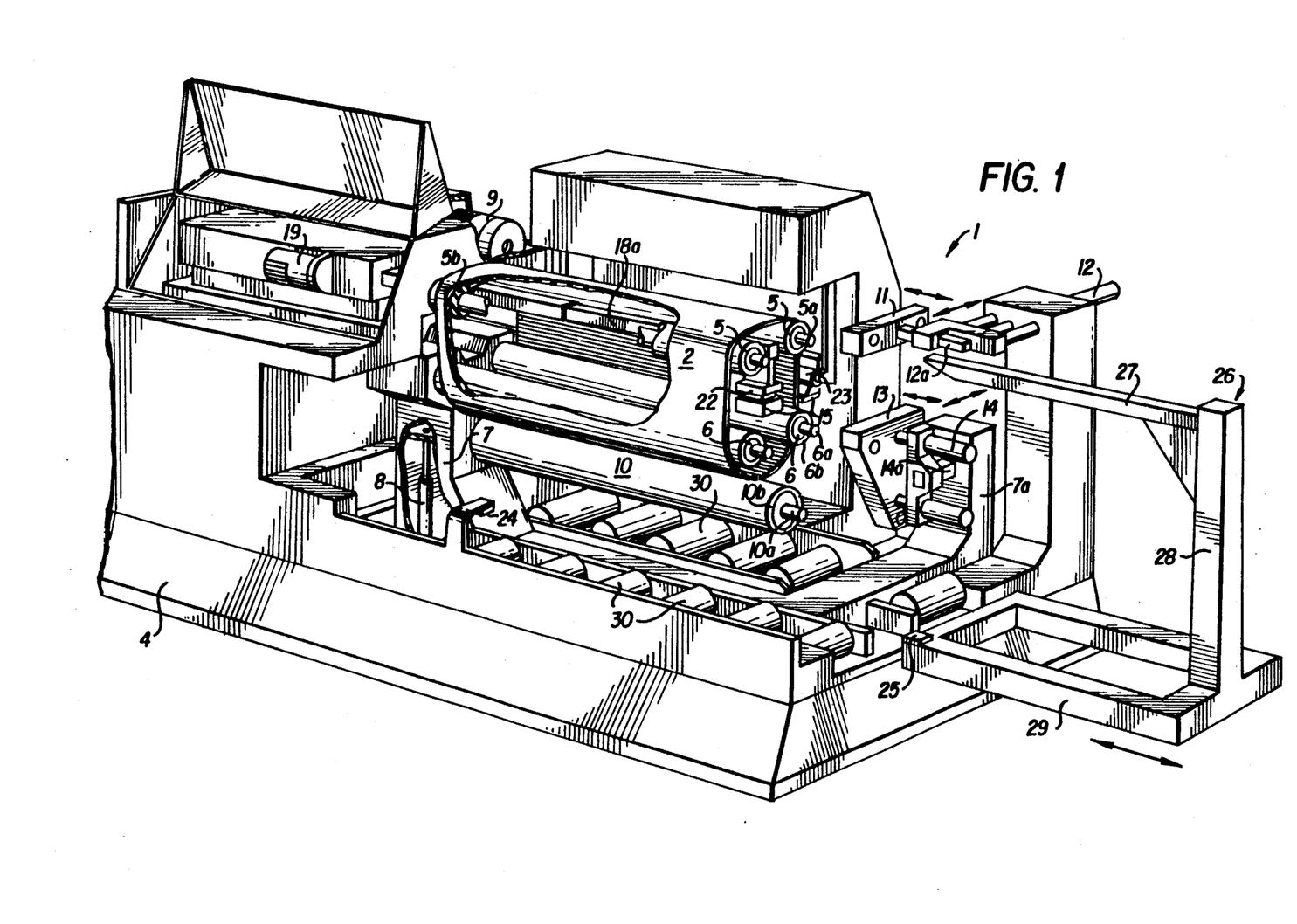
FIG. 1 is a perspective view of an apparatus used for putting into practice the process of the invention on toothed sleeves for the manufacture of toothed belts.

Referring to the drawings and in particular to FIG. 1 an apparatus for identifying the presence of structural cavities in sleeves for the manufacture of driving belts in accordance with the invention has been generally denoted by reference numeral 1.

In the embodiment described apparatus 1 lends itself to act on sleeves 2 of the type used for the manufacture of toothed belts.

Figure 2:
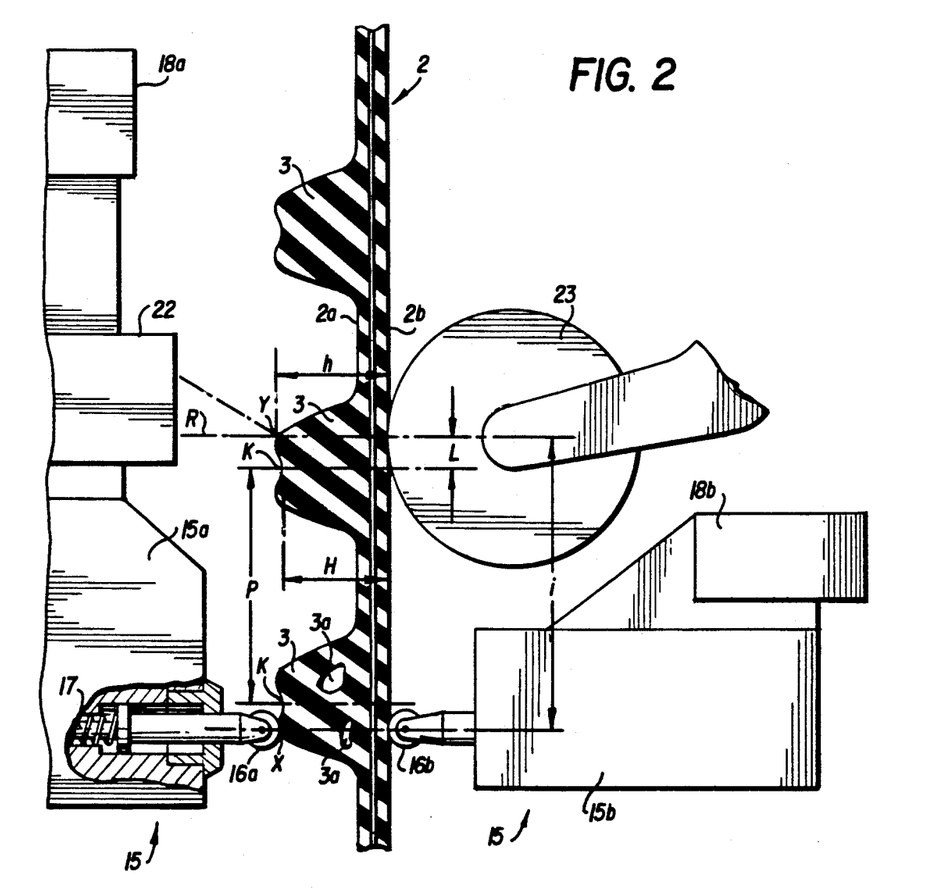
FIG. 2 is a diagrammatic side view of a detail of the apparatus, to an enlarged scale, showing the ultrasonic emitting and receiving member and the reading member in an operating condition.

Each sleeve 2 is provided with a toothed inner surface 2a having a plurality of shaped teeth 3 disposed parallel to one another in side by side relation according to a predetermined spacing "P", (see FIG. 2).

The configuration of the teeth 3 can be various depending upon the purpose of the belt.

In the embodiment shown in FIG. 2 the shape of teeth 3 is as described in the U.S. Pat. No. 4,850,943, the disclosure of which is hereby incorporated by reference.

For various reasons well known to those skilled in the art and discussed above, unacceptable cavities denoted by 3a in FIG. 2 can be present in the sleeve 2 and in particular in the teeth 3.

The presence of these cavities 3a requires discarding of any individual belts that, after the execution of the conventional circumferential-cutting operations on the sleeve 2, exhibit said cavities.

In accordance with the present invention, apparatus 1 lends itself to perform the identification of the structural cavities 3a by a process that, in a preferential solution, essentially comprises the following steps;

a) operatively mounting the sleeve 2 on supporting and handling means;

b) moving the sleeve 2 in a direction transverse to its longitudinal axis;

c) positioning an ultrasonic emitting and receiving member and a reading member in an operating condition on one wall of the sleeve 2;

d) moving the ultrasonic emitting and receiving member and the reading member in a direction parallel to the sleeve axis, so that said emitting and receiving member and reading member act on the sleeve respectively at a first read point and a second read point moving in a helical manner relative to the sleeve axis;

e) repeatedly reading the height of the toothed surface passing under the second read point in order to identify the outline of the transverse extension of the individual teeth 3;

f) timing the interval of time intervening between the different detections of height values carried out during the repeated reading step;

g) identifying the passage under the second read point of at least two characteristic points each belonging to the transverse outline of one of said teeth 3, said characteristic points being spaced apart from each other by a known predetermined amount;

h) measuring the time interval between the passage of said characteristic points under the second read point, to which interval a displacement of the toothed surface 2a equal to said known amount is correlated;

i) assigning a corresponding distance value from one of said characteristic points to each height value detected during step e), based on the time elapsing between the detection of the height value and the detection of the passage of said characteristic point, as well as on the value of the space/time ratio resulting from step h);

j) detecting and processing signals emitted from the ultrasonic emitting and receiving member in order to identify the presence of structural cavities 3a in the sleeve 2;

k) stopping the step e) when the first read point is located in a region of the toothed surface 2a included between two contiguous teeth 3;

l) detecting and storing the position of the ultrasonic emitting and receiving member on the longitudinal extension of the sleeve 2 when the presence of structural cavities 3a has been ascertained.

For the above purpose, apparatus 1 substantially comprises a bed 4 on which supporting means 5, 6, 10 is mounted which is arranged to operatively support the toothed element 2.

In the embodiment shown the supporting means is comprised of at least an upper roller 5 rotatably engaged to the bed 4 and at least a lower roller 6 parallel to the upper roller 5 and operatively engaged to a supporting column 7 movable, upon command of fluid-operated actuators 8 or similar means, to enable the lower roller 6 to move close to and away from the upper roller 5.

In greater detail, in the embodiment shown two upper rollers 5 and two lower rollers 6 are provided and they are disposed in side by side relation along substantially horizontal planes.

Preferably connected to the supporting column 7 is at least one auxiliary lower roller 10, disposed in parallel to and under the lower rollers 6. The auxiliary roller 10 is adapted to be used in place of the lower rollers 6 when the sleeves 2 being worked have a large circumferential extension.

Associated with the supporting means 5, 6, 10 is the motion-imparting means consisting of at least a first motor 9 acting on at least one of the upper rollers 5 to impart a continuous movement to the sleeve 2 in a direction substantially perpendicular to the longitudinal extension of the teeth 3 provided thereon.

As shown in FIG. 1, each of the supporting rollers 5, 6, 10 is provided with a coating layer made of elastomeric material 5b, 6b, 10b in order to ensure a firm grip on the toothed surface 2a and an easy adaptability to the different types of sleeves 2 being worked.

At least one of the ends 5a of each upper roller 5 can be operatively engaged by a first removable support 11 slidably guided relative to the bed 4 and laterally movable apart from the upper rollers, with two degrees of freedom upon command, for example, by fluid-operated cylinders 12 and 12A or the like, to enable the support unit 11 to be moved out of the way of an incoming sleeve 2 to be engaged about the rollers, as diagrammatically shown in FIG. 1.

In the same manner, at least one of the ends 6a, 10a of each of the lower rollers 6 and auxiliary roller 10 can be operatively engaged by a second removable support 13 connected with two degrees of freedom to a side extension 7a of the supporting column 7 and movable laterally apart from the lower rollers upon command, for example by respective actuators 14 and 14A to enable support 13 to be similarly moved.

Apparatus 1 is provided with at least an ultrasonic emitting and receiving member, generally denoted by 15, designed to operate through the sleeve 2 at a first read point "X", (see FIG. 2) in order to detect the presence of structural cavities 3a.

In greater detail, and with reference to FIG. 2, the ultrasonic emitting and receiving member 15, known per se and therefore not described in detail, comprises an ultrasonic emitting part 15a and an ultrasonic receiving part 15b facing each other in mutual alignment and acting by means of respective rollers 16a, 16b in sliding contact relationship on the inner surface 2a and the outer surface 2b respectively, or in any case two opposite surfaces, of the sleeve 2.

Preferably at least the emitting part 15a is submitted to an elastic thrust action upon command of a preloading spring 17 ensuring contact thereof with the outline of the teeth 3.

The emitting part 15a and the receiving part 15b are fastened to respective telescopic bars 18a, 18b (see FIGS. 1 and 2) simultaneously extensible upon command of second motion imparting means consisting for example of at least a threaded bar, not shown and known and conventional, set in rotation by a second motor 19.

The cooperation between the second motor 19 and said threaded bar imparts a continuous translatory movement to the emitting and receiving member, 15 in a direction parallel to the sleeve axis and, therefore, also parallel to the longitudinal extension of the teeth 3.

The ultrasonic emitting and receiving member 15 is capable of sending, by means of the emitting part 15a, ultrasonic signals of an appropriate frequency through the sleeve 2 towards the receiving part 15b.

It is preferably provided that the frequency of the ultrasonic waves should have a value in the range of 0.3 MHz to 0.5 MHz.

The receiving part 15b in turn is capable of sensing the signals sent from the emitting part 15a and consequently emit electric signals correlated with the ultrasonic reception signal.

In the absence of structural discontinuities in the sleeve 2, the ultrasonic waves easily pass through the elastomeric material interposed between the emitting part 15a and the receiving part 15b and can be therefore clearly sensed by the receiving part.

If on the contrary one or more structural cavities 3a are incorporated in the elastomeric material in the regions passed through by the ultrasonic waves, that is at the first read point "X", the travel of the ultrasonic waves is greatly hindered and, as a result, said waves will not be senses by the receiving part 15a or will be sensed to a very reduced degree.

Figures 3, 4:
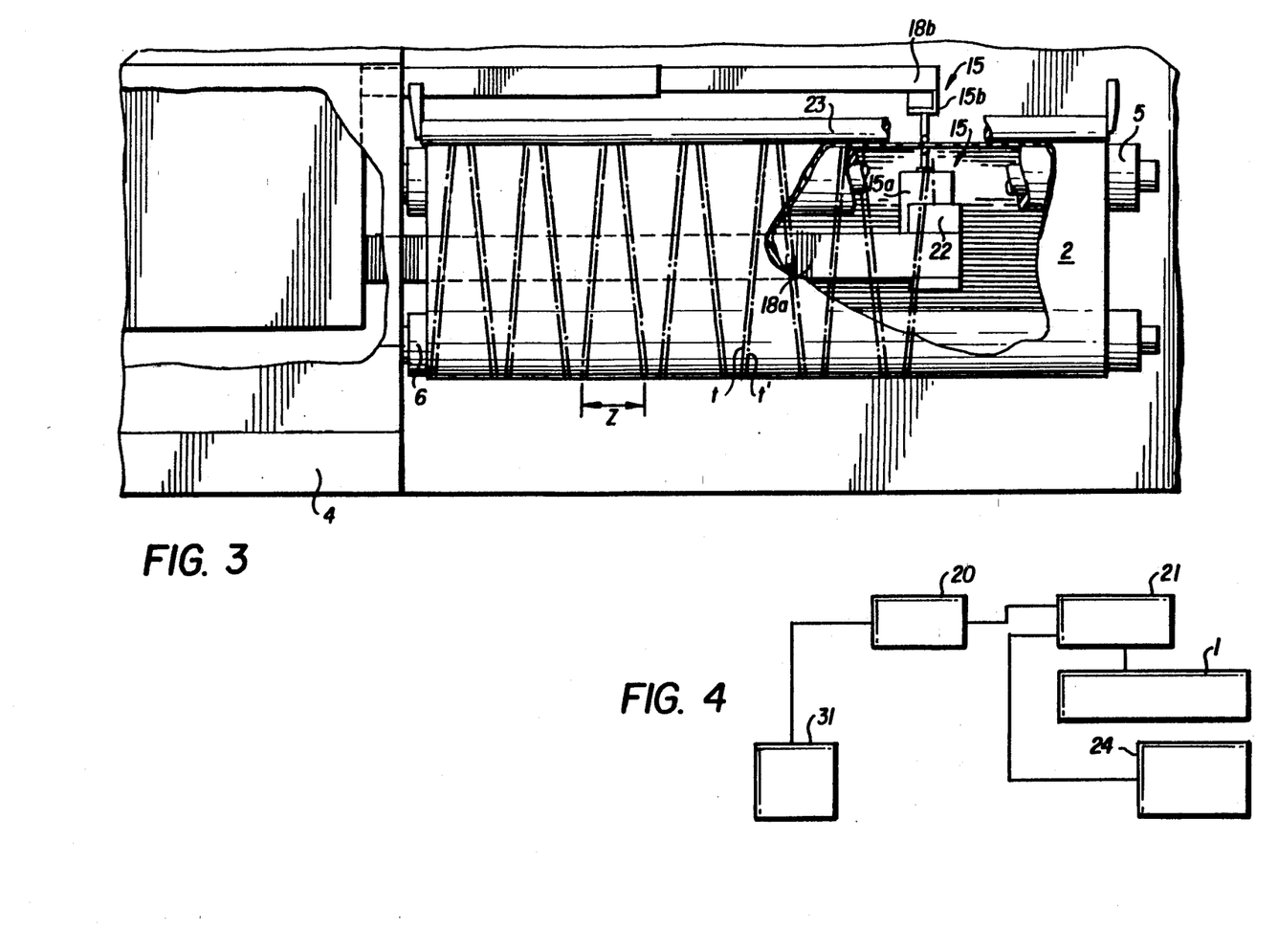
FIG. 3 is fragmentary diagrammatic top view showing the structure of the ultrasonic emitting and receiving member and the reading member, as well as the path of the relative motion between said members and the sleeve.
FIG. 4 is a block diagram showing the operating principle on which the apparatus of the invention is based.

The emitting and receiving member 15 are connected to an electronic processing unit 20.

An electronic control box 21 (FIG. 4) of the type commonly named PLC, controls the sequential operation of the various members associated with apparatus 1 (motors 9, 19, actuator cylinders 8, 12, 14, and so on).

The processing unit 20, preferably consisting of a conventional personal computer, in accordance with modalities to be clarified in the following, processes signals received by the ultrasonic emitting and receiving member 15 in order to identify the position of the structural cavities 3a on the longitudinal extension of the sleeve 2.

In a preferred embodiment, combined with the ultrasonic emitting and receiving member 15 is at least a reading member 22, preferably of the laser beam type, fastened to one end of the telescopic bar 18a engaging the emitting part 15a.

The reading member 22, not described in detail and known per se, sends a light beam "R" onto the toothed surface 2a of the sleeve 2 and, by picking up the reflected light from the struck surface at a second read point "Y" adjacent the first reading point "X", is capable of emitting electric signals correlated to the distance between the reading member and the second read point "Y" struck by the light beam "R".

A freely rotating locating roller 23, disposed parallel to the movement direction of the reading member 22, acts on the outer surface 2b of the sleeve 2 in order to keep said surface to a predetermined distance relative to the reading member.

Preferably, within the general operation of apparatus 1, the reading member 22 which is connected to the electronic processing unit 20 as well upon interposition of the electronic control box 21, is used to inspect the geometrical configuration of the toothed surface 2a, in accordance with a process, which is described in a co-pending patent U.S. application Ser. No. 07/792,880 as already above identified under the heading "Cross Reference to Related Applications" and specifically incorporated herein by reference. For the purpose, the processing unit 20 processes signals received from the reading member 22 in order to draw data relating to the geometrical configuration of the toothed surface 2a therefrom, which data are then compared with theoretical geometric parameters previously stored in the processing unit.

As regards, on the contrary, the cooperation with the ultrasonic emitting and receiving member 15, the reading member 22 is used to enable the electronic processing unit 20 to know the position of the first read point "X", instant by instant, on the outline of the toothed surface 2a.

As will be more clearly understood in the following, this expedient is intended to permit the processing unit 20 to disenable alternatively either the emission or the reception of signals by the ultrasonic emitting and receiving member 15 each time the first read point "X" is located in a region of the toothed surface 2a included between two contiguous teeth 3. The disenabling area in the longitudinal section of the belt in FIG. 2 can be identified by the distance between the points of two teeth in the belt determined by the meeting between the connecting radius at the tooth root and the beginning of the flank.

Theoretical geometric parameters corresponding to the toothed surfaces 2a of different types of sleeves 2 produced in the factory in which apparatus 1 is installed are input to the memory of the processing unit 20. An individual code is then assigned to the theoretical geometric parameters of each type of toothed surface 2a which code will enable the immediate selective recalling of said parameters for carrying out the operating steps of apparatus 1.

The individual code corresponding to the sleeve 2 being tested is detected by the electronic control box 21 when the sleeve is fitted on the rollers 5, 6.

For the purpose, an automatic read and record head 24 is conventionally interlocked to the electronic control box 21, which head is designed to detect the information recorded on a corresponding proper card 25 associated with a handling support 26 conventionally used to transport the sleeves 2 and the belts subsequently produced between the various work stations inside the factory.

Preferably the head 24 and the card 25 are magnetic.

The above handling support 26 holds the sleeve 2 by means of a bar 27 fastened in cantilevered fashion to a post 28 standing up from a base framework 29.

The handling support 26 lends itself to be operatively engaged along a roller-bed 30 mounted to the lower part of the apparatus bed 4, in order to fit the sleeve 3 on the rollers 5, 6 located close to each other, while the magnetic card 25 is simultaneously brought under the read head 24.

In this situation, the electronic control box 21 can transmit the individual code recorded on the magnetic card 25 carried by the handling support 26, to the processing unit 20.

The sleeve 2 is laid on the upper rollers 5, for example by lowering the roller-bed 30, then the handling support 26 is unthreaded from the sleeve, as shown in FIG. 1, to operatively engage with the ends 5a, 6a, 10a of the upper and lower rollers 5 and 6, 10.

Meanwhile, the processing unit 20 has found in its memory the theoretical geometric parameters corresponding to the individual code signalled to it. Therefore the processing unit 20 causes, through the activation of the electronic control box 21, the lowering of the lower rollers 6, 10 to an extent sufficient to produce a given tensioning of the sleeve 2.

At the end of the lowering an inspection step can be provided, through measuring means associated with the supporting column 7, in order to verify whether the carried out positioning of the lower rollers 6, 10 corresponds to the expected tensioning of the sleeve 2.

At this point, apparatus 1 begins the process for identifying the structural cavities 3a in the sleeve 2, which process, in accordance with the present invention, takes place following the modalities set forth hereinafter.

The processing unit 20 enables the electronic control box 21 to actuate the first motor 9 which, through the upper rollers 5, sets in motion the sleeve 2 in a direction transverse to the extension of the teeth 3 in the example of FIG. 1 that would be a rotary motion of the sleeve 2 about is own axis.

Simultaneously the second motor 19 is actuated as well, and it causes the translation of the ultrasonic emitting and receiving member 15 and the reading member 22 in a direction substantially parallel to the longitudinal extension of the teeth 3, according to a predetermined speed.

Preferably the starting motion point of the emitting and receiving member 15 and the reading member 22 is located laterally apart from the sleeve 2, so that the movement speeds of the sleeve and of said members 15, 22 may be stabilized before the process for the identification of cavities 3a really begins.

When the ultrasonic emitting and receiving member 15 and reading member 22 move within the sleeve 2, the first read point "X" and the second read point "Y" are moved relative to the toothed surface according to respective substantially helical parallel paths "t", "t'" (FIG. 3) the pitch "z" of which is correlated with the ratio existing between the movement speeds of the members 15, 22 and the sleeve itself.

By adjusting these speeds it is possible to obtain helical paths "t", "t'" having the desired pitch "z". The more the pitch "z" of paths "t", "t'" is reduced, the more closely the inspection test is carried out. A satisfactorily close inspection is achieved when the pitch "z" of the helical paths "t", "t'" is lower than or equal to the width of the belts to be produced. In this way, one can in fact be sure that all teeth 3 belonging to each of the belts to be obtained will pass before the read point "X", "Y", in order to be submitted to the inspection test.

As previously stated, in order that the processing unit 20 may be capable of periodically disenabling the ultrasonic emitting and receiving member 15 for the above clarified purposes, it is necessary for the processing unit to know the exact position of the first read point "X" relative to the individual teeth 3.

To this end the processing unit 20, based on signals coming from the reading member 22, identifies the transverse outline of the toothed surface 2a by means of repeated detections of the height "h" exhibited, instant by instant, by the toothed surface at the second read point "Y".

Simultaneously, the processing unit 20 calculates the interval of time intervening between tile different detections of the height values "h".

The processing unit 20 also carries out the identification of the passage, under the second read point "Y", of two identical characteristic points "K" each belonging to the transverse outline of one of the teeth 3. These characteristic points "K" that in the described embodiment are constituted by a recess 3b formed on top of each tooth 3 and having a predetermined height "H", are unmistakably spaced apart from each other by a known amount previously stored in the processing unit 20, which amount is preferably the same as the spacing "P" of teeth 3. By measuring the interval of time between the passage of the two characteristic points "K", the processing unit 20 is capable of establishing the displacement of the toothed surface 2a relative to the read points "X" and "Y" expressed as the space/time ratio resulting when the value of spacing "P" is divided by the value of the interval of time.

Depending upon the value of the emerged space/time ratio, the processing unit 20 assigns to each height value "h" detected during the repeated reading step, a corresponding distance value "L" from one of the characteristic points "K", based on the interval of time intervening between the detection of the height value and the detection of the passage of said characteristic point "K".

By mathematically interpolating the center distance "i" existing between the first and second read points "X" and "Y", the processing unit 20 is capable of knowing the exact frequency of passage of the teeth 3 before the first read point "X" and can consequently stop the cavity detection step carried out by the ultrasonic emitting and receiving member 15 each time the first read point "X" falls on the area of the toothed surface 2a included between two contiguous teeth 3.

For safety purposes, the identification of the interval of time intervening between the passage of the characteristic points "K" is preferably repeated two or three times consecutively, each referring to two different teeth 3, as far as the processing unit 20 finds a constant time value for a predetermined number of times between one measuring and the next one.

At the beginning of the test, the execution of these operating steps entails a temporary disenabling of the ultrasonic emitting and receiving member 15, so that, as a result, cavities 3a that might be present in the first teeth 3 passing under the first read point "X" cannot be identified.

This lack of identification however does not represent a problem in that the unchecked teeth certainly belong to one of the end belts of the sleeve 2 that, as is known, are discarded "a priori".

It is also provided that the operating steps for detecting the space/time ratio be carried out several times at predetermined intervals during the inspection test on the sleeve 2.

In this way, one can be sure that the test result is not impaired by possible variations in the relative speed between the toothed surface 2a and the read points "X" and "Y", caused for example either by uncontrolled variations in the running speed of the first and/or second motor 9, 19, or slight elastic deformations of the sleeve 2 and/or the elastomeric coating layers disposed on the rollers 5, 6, 10, or by an imperfect parallelism between the individual teeth 3 and the direction of movement of the emitting and receiving member 15 and the reading member 22.

When the presence of one or more structural cavities 3a is detected, the processing unit 20 identifies which of the belts to be produced in the following cutting operation on the sleeve 2 will have a defective tooth 3.

For the purpose, the processing unit 20 should preferably know the width of the single belts to be produced and be able to carry out the above operation based on the movement speed of the reading member 22 and the interval of time elapsed from the moment that the identification step by the ultrasonic emitting and receiving member has started to the moment at which the presence of cavities 3a is detected.

During the test all the identified cavities 3a and the positions of the belts corresponding thereto are stored in the processing unit 20.

When, at the end of the test, the handling support 26 is engaged again on the roller-bed 30 in order to pick up the sleeve 2, the processing unit 20 will send signals relating to the position of the cavities 3a to the magnetic card 25, through the electronic control box 21 and the read and record head 24.

Signals input to the magnetic card 25 will enable other automatic machines provided in the belt production cycle to identify and discard the belts that after the subsequent cutting operation of the sleeve, will have defective teeth.

Advantageously, the process in accordance with the invention also enables timely interventions in order to eliminate the causes that have led to the formation of the structural cavities 3a.

For the purpose, the processing unit 20 is provided to be able to transmit all data detected during the test to a processor 31. The processor 31 supervising the operation of the main apparatuses used in the belt production cycle will signal the operating anomaly of the apparatus or apparatuses in which the formation of cavities 3a is supposed to have had origin.

The present invention attains the intended purposes.

In fact, by virtue of the process and apparatus in question the possible presence of cavities 3a can be identified in a very reliable and accurate manner.

In this connection it is to be noted that the inventive apparatus also enables cavities of very reduced sizes and completely incorporated in the elastomeric material to be detected.

In addition the process and apparatus in reference permit suitable and timely interventions on the machines and production processes in which the causes of the defects found in the sleeve structure reside.

Obviously, modifications and variations can be made to the invention as conceived, also depending upon the type of sleeve being worked, all of them falling within the scope of the inventive idea.

For example the emitting member can be replaced by equivalent elements adapted to send signals, waves and the like the intensity of which could be sensed by the receiving member to a different extent depending upon the presence or absence of cavities in the elastomeric material of the belt.

The cited equivalent elements can be, among other things, sources emitting other sorts of waves.

The described method can also apply to the identification of cavities located other than in the teeth, for example on elastomeric portions between the tooth base line and the belt back.

We claim:

1. A process for identifying the presence of structural cavities in elongated sleeves for the manufacture of driving belts, each sleeve having a longitudinal axis and at least one toothed surface with a plurality of generally axially extending shaped teeth which are disposed parallel to one another in side by side relation according to a predetermined spacing P, said process comprising the following steps:
   a) operatively mounting the sleeve on supporting and handling means;
   b) moving the sleeve in a direction transverse to its longitudinal axis;
   c) positioning an ultrasonic emitting and receiving member and a reading member in an operating position on one wall of the sleeve;
   d) moving the ultrasonic emitting and receiving member and the reading member in a helical manner and in a direction parallel to the longitudinal axis of the sleeve, so that said emitting and receiving member and said reading member act on the sleeve at a first read point "X" and a second read point "Y" respectively;
   e) repeatedly reading a height "h" of the toothed surface passing under the second read point "Y" in order to identify an outline of individual teeth;
   f) measuring the interval of time between different detections of height value "h" carried out during the repeated reading step;
   g) identifying passage under the second read point "Y" of at least two characteristic points "K" of each outline of one of said teeth, said characteristic points "K" being spaced apart from each other by a known predetermined amount;
   h) measuring the interval of time between the passage of said characteristic points "K" under the second read point "Y", to which interval a displacement of the toothed surface equal to said known amount is correlated;
   i) assigning a corresponding distance value "L" from one of said characteristic points "K", to each height value "h" detected during step e), based on a time elapsing between a detection of a height value and the detection of the passage of said characteristic point K, as well as on a value of a space/time ratio resulting from step h);
   j) detecting and processing signals emitted from the ultrasonic emitting and receiving member in order to identify the presence of structural cavities in the sleeve;
   k) stopping step e) when the first read point X is located in a region of the toothed surfaced included between two contiguous teeth;
   l) detecting and storing the position of the ultrasonic emitting and receiving member on the longitudinal axis of the sleeve when the presence of structural cavities has been ascertained.

2. A process according to claim 1 including performing step l) by measuring the interval of time between the beginning of step j) and the instant at which one of said structural cavities is detected, said ultrasonic emitting and receiving member being moved at a predetermined speed.

3. A process according to claim 1, in which said known amount corresponds to the distribution spacing P of the teeth.

4. A process according to claim 1, in which said steps for identifying the passage of two characteristic points K and measuring the interval of time elapsing between the passage of said points K are carried out several consecutive times when the detected interval of time is the same for a predetermined number of consecutive timings.

5. An apparatus for identifying the presence of structural cavities in elongated sleeves for the manufacture of driving belts, each sleeve having a longitudinal axis and at least one toothed surface having a plurality of generally axially extending shaped teeth which are disposed parallel to one another in side by side relation according to a predetermined spacing P, said apparatus comprising:

supporting means for operatively engaging a sleeve;
first motion-imparting means cooperating with said supporting means so as to impart a continuous movement to the sleeve in a direction transverse to the longitudinal axis thereof;
at least one ultrasonic emitting and receiving member positioned to operate through the sleeve at a first read point X, for detecting the presence of structural cavities within the sleeve;
at least one reading member positioned to operate adjacent the toothed surface in order to identify an outline of the side extension of the individual teeth through repeated readings of a height h of the toothed surface, which is moving before a second read point Y;
second motion-imparting means acting on the emitting and receiving member and the reading member to impart a translatory movement to said member in a helical manner and in a direction parallel to the longitudinal axis of the sleeve, so that the first read point X and second read point Y move helically relative to said longitudinal axis;
an electronic processing unit operatively connected to the ultrasonic emitting and receiving member as well as to the second motion-imparting means in order to identify the position, on a longitudinal surface of the sleeve, of structural cavities detected by said emitting and receiving member, said processing unit being also operatively connected to the reading member so as to disenable the ultrasonic emitting and receiving member when the first read point X is located in an area of the toothed surface included between two contiguous teeth.

6. An apparatus according to claim 5 in which said supporting means comprises at least one upper supporting roller and at least one lower supporting roller parallel thereto and adapted to be selectively positioned so as to be moved closer to and farther away from each other, in order to operatively engage the sleeve so as to give said sleeve a predetermined tensioning.

7. An apparatus according to claim 6, in which at least some of said supporting rollers are provided with a coating layer of elastomeric material.

8. An apparatus according to claim 6 further comprising a pair of upper rollers and a pair of lower rollers disposed parallel to one another in side by side relation and lying in respective horizontal planes.

9. An apparatus according to claim 6 further comprising at least one auxiliary lower roller disposed under said lower supporting roller.

10. An apparatus according to claim 6 in which said lower supporting roller is operatively engaged to a supporting column movable upon command of actuator means to enable the lower roller to move closer to and farther away from the upper roller.

11. An apparatus according to claim 6 in which each of said upper and lower rollers has at least one end operatively supported by a removable support adapted to be laterally moved apart from the corresponding roller to permit the engagement of a tubular sleeve on said upper and lower rollers.

12. An apparatus according to claim 5 in which said ultrasonic emitting and receiving member comprises an ultrasonic emitting part and an ultrasonic receiving part facing each other in mutual alignment and acting by contact on respectively opposite surfaces of the sleeve.

13. An apparatus according to claim 12, in which at least one of said emitting part and said receiving part has means to cause said part to be in an elastic thrust relation.

14. An apparatus according to claim 5, further comprising at least a freely rotating locating roller disposed parallel to the movement direction of the reading member and acting on an outer surface of the sleeve to keep said surface spaced apart by a predetermined distance from the reading member.

15. An apparatus according to claim 5 further comprising a read and record head operatively connected to said processing unit to transmit an individual code to the processing unit, said code being recorded on a card associated with a handling support transporting the sleeve being worked; supporting rollers for said handling support; theoretical geometric parameters of several different toothed elements being stored in said processing unit.

16. An apparatus according to claim 5 in which said electronic processing unit is operatively connected to a processor in order to inform the processor of the presence of structural cavities identified in the sleeve, said processor being arranged to consequently signal any operating anomalies and to identify such anomalies in relation to apparatuses previously used for the production of the sleeve.

17. An apparatus according to claim 15 in which said processing unit is arranged to record on the card, through the read and record head, the position, on a surface of the sleeve, of the structural cavities present therein.

18. An apparatus according to claim 15 in which said head and card are magnetic.

* * * * *